US005858653A

United States Patent [19]
Duran et al.

[11] Patent Number: 5,858,653
[45] Date of Patent: Jan. 12, 1999

[54] REAGENT AND METHOD FOR ATTACHING TARGET MOLECULES TO A SURFACE

[75] Inventors: Lise W. Duran, Maple Grove; Melvin J. Swanson, Carver; Richard A. Amos, St. Anthony; Sheau-Ping J. Hu, Falcon Heights; Patrick E. Guire, Eden Prairie, all of Minn.

[73] Assignee: SurModics, Inc., Eden Prairie, Minn.

[21] Appl. No.: 940,213

[22] Filed: Sep. 30, 1997

[51] Int. Cl.$^6$ ............................ C12Q 1/68; C07C 49/786; C07C 233/64; C07D 207/404

[52] U.S. Cl. ........................ 435/6; 435/176; 435/180; 436/501; 436/96; 436/112; 436/120; 436/128; 436/905; 548/542; 548/545; 548/546; 560/106; 564/155; 564/192; 568/332; 568/335

[58] Field of Search .................... 435/6, 176, 180; 436/501, 96, 112, 120, 128, 905; 548/542; 560/106; 564/155; 568/332

[56] References Cited

U.S. PATENT DOCUMENTS

| | | | |
|---|---|---|---|
| 4,722,906 | 2/1988 | Guire | 436/501 |
| 4,973,493 | 11/1990 | Guire | 427/2 |
| 4,979,959 | 12/1990 | Guire | 623/66 |
| 5,002,582 | 3/1991 | Guire et al. | 623/66 |
| 5,217,492 | 6/1993 | Guire et al. | 623/11 |
| 5,414,075 | 5/1995 | Swan et al. | 568/333 |
| 5,510,084 | 4/1996 | Cros et al. | 422/104 |
| 5,512,329 | 4/1996 | Guire et al. | 427/508 |
| 5,563,056 | 10/1996 | Swan et al. | 435/180 |
| 5,580,697 | 12/1996 | Keana et al. | 430/296 |
| 5,643,580 | 7/1997 | Subramaniam | 424/400 |
| 5,654,162 | 8/1997 | Guire et al. | 435/7.92 |
| 5,707,818 | 1/1998 | Chudzik et al. | 435/7.93 |
| 5,714,360 | 2/1998 | Swan | 435/174 |

OTHER PUBLICATIONS

"The Development of Microfabricated Arrays of DNA Sequencing and Analysis", O'Donnell–Maloney et al., *TIBTECH* 14:401–407 (1996).

"Instructions—Reacti–Bind™ DNA Coating Solution" Jan. 1997.

"Polymeric Phosphonium Salts as a Novel Class of Cationic Biocides. VII. Synthesis and Antibacterial Activity of Polymeric Phosphonium Salts and Their Model Compounds Containing Long Alkyl Chains", *J. Appl. Polymer Sci.* 53:1237–1244 (1994).

"Rapid detetion of Salmonella subspecies 1 by PCT combined with non–radioactive hybridisation using covalently immobilised oligonucleotide on a microplate", Chevier et al. *FEMS* 10:245, 1995.

"Oriented and Covalent Immobilization of Target Molecules to Solid Supports: Synthesis and Application of a Light–Activatable and Thiol–Reactive Cross–Linking Reagent," Collioud et al., *Bioconjugate Chem.* 1993, vol. 4, pp. 528–536.

Primary Examiner—Johann Richter
Assistant Examiner—Jane C. Oswecki
Attorney, Agent, or Firm—Fredrikson & Byron, P.A.

[57] ABSTRACT

Method and reagent composition for covalent attachment of target molecules, such as nucleic acids, onto the surface of a substrate. The reagent composition includes groups capable of attracting the target molecule as well as groups capable of covalently binding to the target molecule, once attracted. Optionally, the composition can contain photoreactive groups for use in attaching the reagent composition to the surface.

60 Claims, No Drawings

REAGENT AND METHOD FOR ATTACHING TARGET MOLECULES TO A SURFACE

TECHNICAL FIELD

The present invention relates to methods for attaching target molecules such as oligonucleotides (oligos) to a surface, and to compositions for use in such methods. In another aspect, the invention relates to the resultant coated surfaces themselves. In yet another aspect, the invention relates to the use of photochemical and thermochemical means to attach molecules to a surface.

BACKGROUND OF THE INVENTION

The immobilization of deoxyribonucleic acid (DNA) onto support surfaces has become an important aspect in the development of DNA-based assay systems as well as for other purposes, including the development of microfabricated arrays for DNA analysis. See, for instance, "The Development of Microfabricated Arrays of DNA Sequencing and Analysis", O'Donnell-Maloney et al., *TIBTECH* 14:401–407 (1996). Generally, such procedures are carried out on the surface of microwell plates, tubes, beads, microscope slides, silicon wafers or membranes. Certain approaches, in particular, have been developed to enable or improve the likelihood of end-point attachment of a synthetic oligo to a surface. End-point attachment (i.e., with the nucleic acid sequence attached through one or the other terminal nucleotide) is desirable because the entire length of the sequence will be available for hybridization to another nucleic acid sequence. This is particularly advantageous for the detection of single base pair changes under stringent hybridization conditions.

Hybridization is the method used most routinely to measure nucleic acids by base pairing to probes immobilized on a solid support. When combined with amplification techniques such as the polymerase chain reaction (PCR) or ligase chain reaction (LCR), hybridization assays are a powerful tool for diagnosis and research. Microwell plates, in particular, are convenient and useful for assaying relatively large numbers of samples. Several methods have been used for immobilization of nucleic acid probes onto microwell plates. Some of these involve adsorption of unmodified or modified oligos onto polystyrene plates. Others involve covalent immobilization. Various methods have also been used to increase the sensitivity of hybridization assays. Polymeric capture and detection probes have been synthesized and used to obtain sensitivities down to $10^7$ DNA molecules/ml. Another method used branched oligos to increase the sensitivity of hybridization assays. Yet another method used a multi-step antibody-enhanced method. Other types of nucleic acid probes such as ribonucleic acid (RNA), complementary DNA (cDNA) and peptide nucleic acids (PNA's) have also been immobilized onto microwell plates for hybridization of PCR products in diagnostic applications. Furthermore, PCR primers have been immobilized onto microwell plates for solid phase PCR.

Only a relative few approaches to immobilizing DNA, to date, have found their way into commercial products. One such product is known as "NucleoLink™", and is available from Nalge Nunc International (see, e.g., Nunc Tech Note Vol. 3, No. 17). In this product, the DNA is reacted with a carbodiimide to activate 5'-phosphate groups which then react with functional groups on the surface. Disadvantages of this approach are that it requires the extra step of adding the carbodiimide reagent as well as a five hour reaction time for immobilization of DNA, and it is limited to a single type of substrate material.

As another example, Pierce has recently introduced a proprietary DNA immobilization product known as "Reacti-Bind™ DNA Coating Solutions" (see "Instructions—Reacti-Bind™ DNA Coating Solution" 1/1997). This product is a solution that is mixed with DNA and applied to surfaces such as polystyrene or polypropylene. After overnight incubation, the solution is removed, the surface washed with buffer and dried, after which it is ready for hybridization. Although the product literature describes it as being useful for all common plastic surfaces used in the laboratory, it does have some limitations. For example, Applicants were not able to demonstrate useful immobilization of DNA onto polypropylene using the manufacturer's instructions. Furthermore, this product requires large amounts of DNA. The instructions indicate that the DNA should be used at a concentration between 0.5 and 5 $\mu$g/ml.

Similarly, Costar sells a product called "DNA-BIND™" for use in attaching DNA to the surface of a well in a microwell plate (see, e.g., the DNA-BIND™ "Application Guide"). The surface of the DNA-BIND™ plate is coated with an uncharged, nonpolymeric, low molecular weight, heterobifunctional reagent containing an N-oxysuccinimide (NOS) reactive group. This group reacts with nucleophiles such as primary amines. The heterobifunctional coating reagent also contains a photochemical group and spacer arm which covalently links the reactive group to the surface of the polystyrene plate. Thereafter, amine-modified DNA can be covalently coupled to the NOS surface. The DNA is modified by adding a primary amine either during the synthesis process to the nascent oligomer or enzymatically to the preformed sequence. Since the DNA-BIND™ product is polystyrene based, it is of limited use for those applications that require elevated temperatures such as thermal cycling.

These various products may be useful for some purposes, or under certain circumstances, but all tend to suffer from one or more drawbacks and constraints. In particular, they either tend to require large amounts of oligo, render background noise levels that are unsuitably high and/or lack versatility.

It would be highly desirable to be able to attach molecules such as oligos to a surface in a manner that avoids some or all of the drawbacks of these previous approaches.

SUMMARY OF THE INVENTION

The present invention provides a method and reagent composition for covalent attachment of target molecules onto the surface of a substrate, such as microwell plates, tubes, beads, microscope slides, silicon wafers or membranes. In a preferred embodiment, the method and composition are used to immobilize nucleic acid probes onto plastic materials such as microwell plates, e.g., for use in hybridization assays. Microwell plates, for instance, can be prepared from a variety of materials, including but not limited to polystyrene, polycarbonate, polyvinyl chloride and polypropylene, and coated with a reagent of the invention. The reagent composition can then be used to both attract and covalently attach a nucleic acid, which in turn can be used to hybridize to its complementary strand.

A reagent composition of the invention contains thermochemically reactive groups (i.e., groups having a reaction rate dependent on temperature) and attractive groups. Optionally, and preferably, the composition can also contain photoreactive groups. Additionally, the reagent may comprise one or more hydrophilic polymers, to which the thermochemically reactive, attractive and/or photoreactive groups can be pendent. The photoreactive groups (alternatively referred to herein as "photogroups") can be used, for instance, to attach reagent molecules to the surface of the support upon the application of a suitable energy source such as light. The thermochemically reactive groups, in turn, can be used to form covalent bonds with appropriate and complementary functional groups on the target molecule. Generally, the reagent molecules will first be attached to the surface by activation of the photogroups, thereafter the target molecule, (e.g., an oligo) is attracted to the bound reagent, largely due to ionic interactions between attractive (e.g., ionic) groups on the bound reagent and oppositely charged groups on the target. Once attracted to the bound reagent, and in turn to the surface, the target molecule can be thermochemically coupled to the bound reagent by reaction between the reactive groups of the bound reagent and appropriate functional groups on the target molecule. The thermochemically reactive groups and the ionic groups can either be on the same polymer or on different polymers that are coimmobilized onto the surface.

While not intending to be bound by theory, it appears that the presence of ionic groups, e.g., cationic groups such as quaternary ammonium groups or protonated (i.e., acidified) tertiary amines, serve to attract the nucleic acid sequence to the surface by means of electrostatic and other forces. This attraction, in turn, enhances the ability of the reactive groups to efficiently couple with corresponding reactive groups on the nucleic acid sequence. Optionally, and preferably, the target molecule can be prepared or provided with finctional groups tailored to reactive groups of the reagent molecule. During their synthesis, for instance, the oligos can be prepared with functional groups such as amine and sulfhydryl groups.

The invention further provides a method of attaching a target molecule, such as an oligo, to a surface, by employing a reagent as described herein. In turn, the invention provides a surface having nucleic acids attached thereto by means of such a reagent, as well as a material (e.g., microwell plate) that provides such a surface.

In yet another aspect, the invention provides a composition comprising a reagent(s) of this invention in combination with a target molecule that contains one or more functional groups reactive with the thermochemically reactive group(s) of the reagent.

An example of a particularly preferred reagent, for instance, is one described herein as a "photopolyQuat", in which a plurality of photo groups and a plurality of cationic groups (in the form of quaternary ammonium groups) are attached to a hydrophilic polymer backbone. Such a reagent provides exceptional versatility, by being coimmobilized with a photopolyNOS at optimal concentrations and ratios for immobilization of target molecules.

Using such reagents, applicants have found that capture probes can be covalently immobilized to a variety of surfaces, including surfaces that would not otherwise adsorb the probes (such as polypropylene and polyvinylchloride). The resulting surfaces provide signals comparable to or better than those obtained with modified oligos adsorbed onto polystyrene or polycarbonate.

The present immobilization reagent and method can be used in amplification methods in a manner that is simpler than those previously reported, and can also provide improved surfaces for the covalent immobilization of nucleophile-derivatized nucleic acids. In addition to immobilized probes for amplification methods and hybridization assays, the reagents of this invention may provide improved nucleic acid immobilization for solid phase sequencing and for immobilizing primers for PCR and other amplification techniques.

DETAILED DESCRIPTION

A preferred reagent composition of the present invention comprises a hydrophilic backbone bearing one or more ionic groups having the ability to attract a corresponding target molecule, together with one or more photoreactive groups useful for attaching the reagent to a surface, and one or more thermochemically reactive groups useful for forming a covalent bond with the corresponding reactive group of the target molecule. Optionally and preferably, the composition can include the use of two or more different reagent molecules, the first comprising a hydrophilic backbone bearing one or more ionic groups having the ability to attract a corresponding target molecule, together with one or more photoreactive groups useful for attaching the reagent to a surface. The second reagent molecule comprising a hydrophilic backbone bearing one or more thermochemically reactive groups useful for forming a covalent bond with the corresponding functional group of the target molecule, together with one or more photoreactive groups useful for attaching the reagent to a surface. Optionally, only one of the reagent molecules is required to have the photoreactive groups since that reagent is capable of coimmobilizing the second polymer through photochemical crosslinking. In this case, however, the reagent molecule must have two or more photoreactive groups in order to provide coupling to the surface and to the second polymer.

In a further extension of the invention, it is not necessary that both the ionic group and the thermochemically reactive group be incorporated as part of a hydrophilic polymer. A small heterobifunctional molecule, for instance, having one or more photoreactive groups and one or more thermochemically reactive groups, separated by a suitable spacer, can be used with a photoreactive hydrophilic polymer having the ionic group to accomplish the immobilization of nuclei acid sequences. Conversely, a heterobifinctional molecule having one or more photoreactive group and one or more ionic groups separated by a suitable spacer can be used with a photoreactive hydrophilic polymer having the thermochemically reactive group. Although preferred, the use of a hydrophilic polymeric backbone is merely optional, since both ionic groups and thermochemically reactive groups can be incorporated as two separate photoreactive heterobifinctional molecules or as a single photoreactive molecule bearing both types of groups.

In another embodiment of the invention, it is possible to immobilize nucleic acid sequences without the use of the photoreactive group. For instance, the surface of the material to be coated can be provided with thermochemically reactive groups, which can be used to immobilize hydrophilic polymers having ionic and thermochemically reactive groups as described above. For example, a surface may be treated with an ammonia plasma to introduce a limited number of reactive amines on the surface of the material. If this surface is then treated with a hydrophilic polymer having both the quaternary ammonium group as well as NOS groups, then the polymer can be immobilized through reaction of the NOS groups with amines on the surface. Preferably, the NOS groups on the polymer are in excess relative to the amines on the surface to insure that a sufficient number of these thermochemically reactive groups remain following the immobilization to allow coupling with the nucleic acid sequence.

Those skilled in the art, given the present description, will be able to identify and select suitable ionic groups depending on the type of target molecule of interest. Target molecules include, but are not limited to, plasmid DNA, cosmid DNA, bacteriophage DNA, genomic DNA (includes, but not limited to yeast, viral, bacterial, mammalian, insect), RNA, cDNA, PNA, and oligos.

Suitable ionic groups include quaternary ammonium salts, protonated tertiary amines and other cationic groups such as phosphonium compounds. Also included are tertiary amine groups capable of being protonated when placed in an acid environment. Quaternary ammonium salts include alkyl quaternary ammonium compounds, such as [3-(methacryloylamino)propyl]trimethylammonium chloride (MAPTAC), as well as aromatic quaternary ammonium groups such as pyridinium compounds. Phosphonium compounds include polymers prepared from monomers such as tributyl(4-vinylbenzyl)phosphonium chloride, and are described in *J. AppL Polymer Sci.* 53:1237 (1994), the disclosure of which is also incorporated by reference.

A polymeric backbone can be either synthetic or naturally occurring, and is preferably a synthetic polymer selected from the group consisting of oligomers, homopolymers, and copolymers resulting from addition or condensation polymerization. Naturally occurring polymers, such as polysaccharides, polypeptides can be used as well. Preferred backbones are biologically inert, in that they do not provide a biological function that is inconsistent with, or detrimental to, their use in the manner described.

Such polymer backbones can include acrylics such as those polymerized from hydroxyethyl acrylate, hydroxyethyl methacrylate, glyceryl acrylate, glyceryl methacrylate, acrylamide and methacrylamide, vinyls such as polyvinyl pyrrolidone and polyvinyl alcohol, nylons such as polycaprolactam, polylauryl lactam, polyhexamethylene adipamide and polyhexamethylene dodecanediamide, polyurethanes and polyethylene oxide.

The polymeric backbones of the invention are chosen to provide hydrophilic backbones capable of bearing the desired number and type of ionic groups, photogroups, and thermochemically reactive groups, the combination dependent upon the reagent selected. The polymeric backbone is also selected to provide a spacer between the surface and the various ionic and thermochemically reactive groups. In this manner, the reagent can be bonded to a surface or to an adjacent reagent molecule, to provide the other groups with sufficient freedom of movement to demonstrate optimal activity. The polymer backbones are preferably hydrophilic (e.g., water soluble), with polyacrylamide and polyvinylpyrrolidone being particularly preferred polymers.

Reagents of the invention carry one or more pendent latent reactive (preferably photoreactive) groups covalently bonded to the polymer backbone. Photoreactive groups are defined herein, and preferred groups are sufficiently stable to be stored under conditions in which they retain such properties. See, e.g., U.S. Pat. No. 5,002,582, the disclosure of which is incorporated herein by reference. Latent reactive groups can be chosen that are responsive to various portions of the electromagnetic spectrum, with those responsive to ultraviolet and visible portions of the spectrum (referred to herein as "photoreactive") being particularly preferred.

Photoreactive groups respond to specific applied external stimuli to undergo active specie generation with resultant covalent bonding to an adjacent chemical structure, e.g., as provided by the same or a different molecule. Photoreactive groups are those groups of atoms in a molecule that retain their covalent bonds unchanged under conditions of storage but that, upon activation by an external energy source, form covalent bonds with other molecules.

The photoreactive groups generate active species such as free radicals and particularly nitrenes, carbenes, and excited states of ketones upon absorption of electromagnetic energy. Photoreactive groups may be chosen to be responsive to various portions of the electromagnetic spectrum, and photoreactive groups that are responsive to e.g., ultraviolet and visible portions of the spectrum are preferred and may be referred to herein occasionally as "photochemical group" or "photogroup".

Photoreactive aryl ketones are preferred, such as acetophenone, benzophenone, anthraquinone, anthrone, and anthrone-like heterocycles (i.e., heterocyclic analogs of anthrone such as those having N, O, or S in the 10-position), or their substituted (e.g., ring substituted) derivatives. The functional groups of such ketones are preferred since they are readily capable of undergoing the activation/inactivation/reactivation cycle described herein. Benzophenone is a particularly preferred photoreactive moiety, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source. Photoactivatible aryl ketones such as benzophenone and acetophenone are of particular importance inasmuch as these groups are subject to multiple reactivation in water and hence provide increased coating efficiency. Hence, photoreactive aryl ketones are particularly preferred.

The azides constitute a preferred class of photoreactive groups and include arylazides ($C_6R_5N_3$) such as phenyl azide and particularly 4-fluoro-3-nitrophenyl azide, acyl azides (—CO—$N_3$) such as benzoyl azide and p-methylbenzoyl azide, azido formates (—O—CO—$N_3$) such as ethyl azidoformate, phenyl azidoformate, sulfonyl azides (—$SO_2$—$N_3$) such as benzenesulfonyl azide, and phosphoryl azides $(RO)_2PON_3$ such as diphenyl phosphoryl azide and diethyl phosphoryl azide. Diazo compounds constitute another class of photoreactive groups and include diazoalkanes (—$CHN_2$) such as diazomethane and diphenyldiazomethane, diazoketones (—CO—$CHN_2$) such as diazoacetophenone and 1-trifluoromethyl-1-diazo-2-pentanone, diazoacetates (—O—CO—$CHN_2$) such as t-butyl diazoacetate and phenyl diazoacetate, and beta-keto-alpha-diazoacetates (—CO—$CN_2$—CO—O—) such as t-butyl alpha diazoacetoacetate. Other photoreactive groups include the diazirines (—$CHN_2$) such as 3-trifluoromethyl-3-phenyldiazirine, and ketenes (—CH=C=O) such as ketene and diphenylketene. Photoactivatible aryl ketones such as benzophenone and acetophenone are of particular importance inasmuch as these groups are subject to multiple reactivation in water and hence provide increased coating efficiency.

Upon activation of the photoreactive groups, the reagent molecules are covalently bound to each other and/or to the material surface by covalent bonds through residues of the photoreactive groups. Exemplary photoreactive groups, and their residues upon activation, are shown as follows.

| Photoreactive | Group | Residue Functionality |
|---|---|---|
| aryl azides | amine | R—NH—R' |
| acyl azides | amide | R—CO—NH—R' |
| azidoformates | carbamate | R—O—CO—NH—R' |
| sulfonyl azides | sulfonamide | R—SO$_2$—NH—R' |
| phosphoryl azides | phosphoramide | (RO)$_2$PO—NH—R' |
| diazoalkanes | new C—C bond | |
| diazoketones | new C—C bond and ketone | |
| diazoacetates | new C—C bond and ester | |
| beta-keto-alpha-diazoacetates | new C—C bond and beta-ketoester | |
| aliphatic azo | new C—C bond | |
| diazirines | new C—C bond | |
| ketenes | new C—C bond | |
| photoactivated ketones | new C—C bond and alcohol | |

Those skilled in the art, given the present description, will be able to identify and select suitable thermochemically reactive groups to provide for covalent immobilization of appropriately derivatized nucleic acid sequences. For example, an amino derivatized nucleic acid sequence will undergo a covalent coupling reaction with an activated ester such as a NOS ester to provide an amide linking group. Similar activated esters such p-nitrophenyl and pentafluorophenyl esters would also provide amide links when reacted with amine groups. Those skilled in the art would also recognize numerous other amine-reactive functional groups such as isocyanates, thioisocyanates, carboxylic acid chlorides, epoxides, aldehydes, alkyl halides and sulfonate esters, such as mesylate, tosylate and tresylate, each of which could serve as the thermochemically reactive group.

In another example, the nucleic acid sequence can be derivatized with a sulfhydryl group using techniques well known in the art. The corresponding thermochemically reactive group would be, for example, a maleimide ring structure or an α-iodoacetamide. Either of these structures would react readily to provide a covalent linkage with the sulfhydryl derivatized nucleic acid sequence.

The functionalized polymers of this invention can be prepared by appropriate derivatization of a preformed polymer or, more preferably, by polymerization of a set of comonomers to give the desired substitution pattern. The latter approach is preferred because of the ease of changing the ratio of the various comonomers and by the ability to control the level of incorporation into the polymer. A combination of these two approaches can also be used to provide optimal structures.

In a preferred embodiment, for instance, monomers are prepared having a polymerizable group at one end of the molecule, separated by a spacer group from a photoreactive or thermochemically reactive group at the other end. For example, polymerizable vinyl groups such as acrylamides, acrylates, or maleimides can be coupled through a short hydrocarbon spacer to an activated ester such as a NOS ester or to a photoreactive group such as a substituted benzophenone. These compounds can be prepared and purified using organic synthesis techniques well known to those skilled in the art. Some of desired monomers are commercially available, such as MAPTAC, N-[3-(dimethylamino)propyl] methacrylamide (DMAPMA), and N-(3-aminopropyl) methacrylamide hydrochloride (APMA), these compounds providing quaternary ammonium salts, tertiary amines, and primary amines respectively along the backbone of the polymer.

Copolymers can be prepared from the above monomers as well, using techniques known to those skilled in the art. Preferably, these monomers and copolymers undergo free radical polymerization of vinyl groups using azo initiators such as 2,2'-azobisisobutyronitrile (AIBN) or peroxides such as benzoyl peroxide. The monomers selected for the polymerization are chosen based on the nature of the final polymer product. For example, a photoreactive polymer containing quaternary ammonium groups is prepared from a monomer containing the photoreactive group and a second monomer containing a quaternary ammonium group. A photoreactive polymer containing a NOS group is prepared from a monomer containing the photoreactive group and a second monomer containing the activated NOS ester. A photoreactive polymer containing both quaternary ammonium groups and NOS esters is prepared using all three monomers.

The composition of the final polymer can be controlled by mole ratio of the monomers charged to the polymerization reaction. Typically these functionalized monomers are used at relatively low mole percentages of the total monomer content of the polymerization reaction with the remainder of the composition consisting of a monomer which is neither photoreactive nor thermochemically reactive toward the nucleic acid sequence. Examples of such monomers include, but are not limited to, acrylamide and N-vinylpyrrolidone. Based on the relative reactivities of the monomers used, the distribution of the monomers along the backbone is largely random.

In some cases, the thermochemically reactive group on the backbone of the polymer can itself act as a polymerizable monomer, if present during polymerization, thus requiring the introduction of that group in a second step following the initial formation of the polymer. For example, the preparation of a photoreactive polymer having maleimide along the backbone can be accomplished by an initial preparation of a polymer containing both photoreactive groups and amine groups using the techniques described above, followed by reaction of the amine groups with a heterobifunctional molecule containing a maleimide group and an isocyanate connected by a short hydrocarbon spacer. A wide variety of such polymer modification techniques are available using typical organic reactions known to those skilled in the art.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight. Structures of the various "Compounds" identified throughout these Examples can be found in Table 9 included below.

EXAMPLES

Example 1

Preparation of 4-Benzoylbenzoyl Chloride (BBA-Cl) (Compound I)

4-Benzoylbenzoic acid (BBA), 1.0 kg (4.42 moles), was added to a dry 5 liter Morton flask equipped with reflux condenser and overhead stirrer, followed by the addition of 645 ml (8.84 moles) of thionyl chloride and 725 ml of toluene. Dimethylformamide, 3.5 ml, was then added and the mixture was heated at reflux for 4 hours. After cooling, the solvents were removed under reduced pressure and the residual thionyl chloride was removed by three evaporations using 3×500 ml of toluene. The product was recrystallized from 1:4 toluene: hexane to give 988 g (91% yield) after drying in a vacuum oven. Product melting point was 92°–94° C. Nuclear magnetic resonance (NMR) analysis at 80 MHz ($^1$H NMR (CDCl$_3$)) was consistent with the desired product: aromatic protons 7.20–8.25 (m, 9 H). All chemical shift values are in ppm downfield from a tetramethylsilane internal standard. The final compound was stored for use in the preparation of a monomer used in the synthesis of photoactivatable polymers as described, for instance, in Example 3.

Example 2

Preparation of N-(3-Aminopropyl)methacrylamide Hydrochloride (APMA) (Compound II)

A solution of 1,3-diaminopropane, 1910 g (25.77 moles), in 1000 ml of CH$_2$Cl$_2$ was added to a 12 liter Morton flask and cooled on an ice bath. A solution of t-butyl phenyl carbonate, 1000 g (5.15 moles), in 250 ml of CH$_2$Cl$_2$ was then added dropwise at a rate which kept the reaction temperature below 15° C. Following the addition, the mixture was warmed to room temperature and stirred 2 hours. The reaction mixture was diluted with 900 ml of CH$_2$Cl$_2$ and 500 g of ice, followed by the slow addition of 2500 ml of 2.2N NaOH. After testing to insure the solution was basic, the product was transferred to a separatory funnel and the organic layer was removed and set aside as extract #1. The aqueous was then extracted with 3×1250 ml of CH$_2$Cl$_2$, keeping each extraction as a separate fraction. The four organic extracts were then washed successively with a single 1250 ml portion of 0.6N NaOH beginning with fraction #1 and proceeding through fraction #4. This wash procedure was repeated a second time with a fresh 1250 ml portion of 0.6N NaOH. The organic extracts were then combined and dried over Na$_2$SO$_4$. Filtration and evaporation of solvent to a constant weight gave 825 g of N-mono-t-BOC-1,3-diaminopropane which was used without further purification.

A solution of methacrylic anhydride, 806 g (5.23 moles), in 1020 ml of CHCl$_3$ was placed in a 12 liter Morton flask equipped with overhead stirrer and cooled on an ice bath. Phenothiazine, 60 mg, was added as an inhibitor, followed by the dropwise addition of N-mono-t-BOC-1,3-diaminopropane, 825 g (4.73 moles), in 825 ml of CHCl$_3$. The rate of addition was controlled to keep the reaction temperature below 10° C. at all times. After the addition was complete, the ice bath was removed and the mixture was left to stir overnight. The product was diluted with 2400 ml of water and transferred to a separatory funnel. After thorough mixing, the aqueous layer was removed and the organic layer was washed with 2400 ml of 2N NaOH, insuring that the aqueous layer was basic. The organic layer was then dried over Na$_2$SO$_4$ and filtered to remove drying agent. A portion of the CHCl$_3$ solvent was removed under reduced pressure until the combined weight of the product and solvent was approximately 3000 g. The desired product was then precipitated by slow addition of 11.0 liters of hexane to the stirred CHCl$_3$ solution, followed by overnight storage at 4° C. The product was isolated by filtration and the solid was rinsed twice with a solvent combination of 900 ml of hexane and 150 ml of CHCl$_3$. Thorough drying of the solid gave 900 g of N-[N'-(t-butyloxycarbonyl)-3-aminopropyl]-methacrylamide, m.p. 85.8° C. by DSC. Analysis on an NMR spectrometer was consistent with the desired product: $^1$H NMR (CDCl$_3$) amide NH's 6.30–6.80, 4.55–5.10 (m, 2 H), vinyl protons 5.65, 5.20 (m, 2 H), methylenes adjacent to N 2.90–3.45 (m, 4 H), methyl 1.95 (m, 3 H), remaining methylene 1.50–1.90 (m, 2 H), and t-butyl 1.40 (s, 9 H).

A 3-neck, 2 liter round bottom flask was equipped with an overhead stirrer and gas sparge tube. Methanol, 700 ml, was added to the flask and cooled on an ice bath. While stirring, HCl gas was bubbled into the solvent at a rate of approximately 5 liters/minute for a total of 40 minutes. The molarity of the final HCl/MeOH solution was determined to be 8.5M by titration with 1N NaOH using phenolphthalein as an indicator. The N-[N'-(t-butyloxycarbonyl)-3-aminopropyl] methacrylamide, 900 g (3.71 moles), was added to a 5 liter Morton flask equipped with an overhead stirrer and gas outlet adapter, followed by the addition of 1150 ml of methanol solvent. Some solids remained in the flask with this solvent volume. Phenothiazine, 30 mg, was added as an inhibitor, followed by the addition of 655 ml (5.57 moles) of the 8.5M HCl/MeOH solution. The solids slowly dissolved with the evolution of gas but the reaction was not exothermic. The mixture was stirred overnight at room temperature to insure complete reaction. Any solids were then removed by filtration and an additional 30 mg of phenothiazine were added. The solvent was then stripped under reduced pressure and the resulting solid residue was azeotroped with 3×1000 ml of isopropanol with evaporation under reduced pressure. Finally, the product was dissolved in 2000 ml of refluxing isopropanol and 4000 ml of ethyl acetate were added slowly with stirring. The mixture was allowed to cool slowly and was stored at 4° C. overnight. Compound II was isolated by filtration and was dried to constant weight, giving a yield of 630 g with a melting point of 124.7° C. by DSC. Analysis on an NMR spectrometer was consistent with the desired product: $^1$H NMR (D$_2$O) vinyl protons 5.60, 5.30 (m, 2 H), methylene adjacent to amide N 3.30 (t, 2 H), methylene adjacent to amine N 2.95 (t, 2 H), methyl 1.90 (m, 3 H), and remaining methylene 1.65–2.10 (m, 2 H). The final compound was stored for use in the preparation of a monomer used in the synthesis of photoactivatable polymers as described, for instance, in Example 3.

Example 3

Preparation of N-[3-(4-Benzoylbenzamido)propyl] methacrylamide (BBA-APMA) (Compound III)

Compound II 120 g (0.672 moles), prepared according to the general method described in Example 2, was added to a dry 2 liter, three-neck round bottom flask equipped with an overhead stirrer. Phenothiazine, 23–25 mg, was added as an inhibitor, followed by 800 ml of chloroform. The suspension was cooled below 10° C. on an ice bath and 172.5 g (0.705 moles) of Compound I, prepared according to the general method described in Example 1, were added as a solid. Triethylamine, 207 ml (1.485 moles), in 50 ml of chloroform was then added dropwise over a 1–1.5 hour time period. The ice bath was removed and stirring at ambient temperature was continued for 2.5 hours. The product was then washed with 600 ml of 0.3N HCl and 2×300 ml of 0.07N HCl. After drying over sodium sulfate, the chloroform was removed under reduced pressure and the product was recrystallized twice from 4:1 toluene: chloroform using 23–25 mg of phenothiazine in each recrystallization to prevent polymerization. Typical yields of Compound III were 90% with a melting point of 147°–151° C. Analysis on an NMR spectrometer was consistent with the desired product: $^1$H NMR (CDCl$_3$) aromatic protons 7.20–7.95 (m, 9 H), amide NH 6.55 (broad t, 1 H), vinyl protons 5.65, 5.25 (m, 2 H), methylenes adjacent to amide N's 3.20–3.60 (m, 4 H), methyl 1.95 (s, 3 H), and remaining methylene 1.50–2.00 (m, 2 H). The final compound was stored for use in the synthesis of photoactivatable polymers as described, for instance, in Examples 9–11.

Example 4

Preparation of N-Succinimidyl 6-Maleimidohexanoate (MAL-EAC-NOS) (Compound Iv)

A functionalized monomer was prepared in the following manner, and was used as described in Examples 9 and 12 to introduce activated ester groups on the backbone of a polymer. 6-Aminohexanoic acid, 100.0 g (0.762 moles), was dissolved in 300 ml of acetic acid in a three-neck, 3 liter flask equipped with an overhead stirrer and drying tube. Maleic anhydride, 78.5 g (0.801 moles), was dissolved in 200 ml of acetic acid and added to the 6-aminohexanoic acid solution. The mixture was stirred one hour while heating on a boiling water bath, resulting in the formation of a white solid. After cooling overnight at room temperature, the solid was collected by filtration and rinsed with 2×50 ml of hexane. After drying, the typical yield of the (Z)-4-oxo-5-aza-2-undecendioic acid was 158–165 g (90–95%) with a melting point of 160°–165° C. Analysis on an NMR spectrometer was consistent with the desired product: $^1$H NMR (DMSO-$d_6$) amide proton 8.65–9.05 (m, 1 H), vinyl protons 6.10, 6.30 (d, 2 H), methylene adjacent to nitrogen 2.85–3.25 (m, 2 H), methylene adjacent to carbonyl 2.15 (t, 2 H), and remaining methylenes 1.00–1.75 (m, 6 H).

(Z)-4-Oxo-5-aza-2-undecendioic acid, 150.0 g (0.654 moles), acetic anhydride, 68 ml (73.5 g, 0.721 moles), and phenothiazine, 500 mg, were added to a 2 liter three-neck round bottom flask equipped with an overhead stirrer. Triethylamine, 91 ml (0.653 moles), and 600 ml of THF were added and the mixture was heated to reflux while stirring. After a total of 4 hours of reflux, the dark mixture was cooled to <60° C. and poured into a solution of 250 ml of 12N HCl in 3 liters of water. The mixture was stirred 3 hours at room temperature and then was filtered through a filtration pad (Celite 545, J. T. Baker, Jackson, Tenn.) to remove solids. The filtrate was extracted with 4×500 ml of chloroform and the combined extracts were dried over sodium sulfate. After adding 15 mg of phenothiazine to prevent polymerization, the solvent was removed under reduced pressure. The 6-maleimidohexanoic acid was recrystallized from 2:1 hexane: chloroform to give typical yields of 76–83 g (55–60%) with a melting point of 81°–85° C. Analysis on a NMR spectrometer was consistent with the desired product: $^1$H NMR (CDCl$_3$) maleimide protons 6.55 (s, 2 H), methylene adjacent to nitrogen 3.40 (t, 2 H), methylene adjacent to carbonyl 2.30 (t, 2 H), and remaining methylenes 1.05–1.85 (m, 6 H).

The 6-maleimidohexanoic acid, 20.0 g (94.7 mmol), was dissolved in 100 ml of chloroform under an argon atmosphere, followed by the addition of 41 ml (0.47 mol) of oxalyl chloride. After stirring for 2 hours at room temperature, the solvent was removed under reduced pressure with 4×25 ml of additional chloroform used to remove the last of the excess oxalyl chloride. The acid chloride was dissolved in 100 ml of chloroform, followed by the addition of 12.0 g (0.104 mol) of N-hydroxysuccinimide and 16.0 ml (0.114 mol) of triethylamine. After stirring overnight at room temperature, the product was washed with 4×100 ml of water and dried over sodium sulfate. Removal of solvent gave 24.0 g of product (82%) which was used without further purification. Analysis on an NMR spectrometer was consistent with the desired product: $^1$H NMR (CDCl$_3$) maleimide protons 6.60 (s, 2 H), methylene adjacent to nitrogen 3.45 (t, 2 H), succinimidyl protons 2.80 (s, 4 H), methylene adjacent to carbonyl 2.55 (t, 2 H), and remaining methylenes 1.15–2.00 (m, 6 H). The final compound was stored for use in the synthesis of photoactivatable polymers as described, for instance, in Examples 9 and 12.

Example 5

Preparation of N-Succinimidyl 6-Methacrylamidohexanoate (MA-EAC-NOS) (Compound V)

A functionalized monomer was prepared in the following manner, and was used as described in Example 11 to introduce activated ester groups on the backbone of a polymer. 6-Aminocaproic acid, 4.00 g (30.5 mmol), was placed in a dry round bottom flask equipped with a drying tube. Methacrylic anhydride, 5.16 g (33.5 mmol), was then added and the mixture was stirred at room temperature for four hours. The resulting thick oil was triturated three times with hexane and the remaining oil was dissolved in chloroform, followed by drying over sodium sulfate. After filtration and evaporation, a portion of the product was purified by silica gel flash chromatography using a 10% methanol in chloroform solvent system. The appropriate fractions were combined, 1 mg of phenothiazine was added, and the solvent was removed under reduced pressure. Analysis on an NMR spectrometer was consistent with the desired product: $^1$H NMR (CDCl$_3$) carboxylic acid proton 7.80–8.20 (b, 1 H), amide proton 5.80–6.25 (b, 1 H), vinyl protons 5.20 and 5.50 (m, 2 H), methylene adjacent to nitrogen 3.00–3.45 (m, 2 H), methylene adjacent to carbonyl 2.30 (t, 2 H), methyl group 1.95 (m, 3 H), and remaining methylenes 1.10–1.90 (m, 6 H).

6-Methacrylamidohexanoic acid, 3.03 g (15.2 mmol), was dissolved in 30 ml of dry chloroform, followed by the addition of 1.92 g (16.7 mmol) of N-hydroxysuccinimide and 6.26 g (30.4 mmol) of 1,3-dicyclohexylcarbodiimide. The reaction was stirred under a dry atmosphere overnight at room temperature. The solid was then removed by filtration and a portion was purified by silica gel flash chromatography. Non-polar impurities were removed using a chloroform solvent, followed by elution of the desired product using a 10% tetrahydrofuran in chloroform solvent. The appropriate fractions were pooled, 0.2 mg of phenothiazine were added, and the solvent was evaporated under reduced pressure. This product, containing small amounts of 1,3-dicyclohexylurea as an impurity, was used without further purification. Analysis on an NMR spectrometer was consistent with the desired product: $^1$H NMR (CDCl$_3$) amide proton 5.60–6.10 (b, 1 H), vinyl protons 5.20 and 5.50 (m, 2 H), methylene adjacent to nitrogen 3.05–3.40 (m, 2 H), succinimidyl protons 2.80 (s, 4 H), methylene adjacent to carbonyl 2.55 (t, 2 H), methyl 1.90 (m, 3 H), and remaining methylenes 1.10–1.90 (m, 6 H). The final compound was stored for use in the synthesis of photoactivatable polymers as described, for instance, in Example 11.

Example 6

Preparation of 4-Bromomethylbenzophenone (BMBP) (Compound VI)

4-Methylbenzophenone, 750 g (3.82 moles), was added to a 5 liter Morton flask equipped with an overhead stirrer and dissolved in 2850 ml of benzene. The solution was then heated to reflux, followed by the dropwise addition of 610 g (3.82 moles) of bromine in 330 ml of benzene. The addition rate was approximately 1.5 ml/min and the flask was illuminated with a 90 watt (90 joule/sec) halogen spotlight to initiate the reaction. A timer was used with the lamp to provide a 10% duty cycle (on 5 seconds, off 40 seconds), followed in one hour by a 20% duty cycle (on 10 seconds, off 40 seconds). At the end of the addition, the product was analyzed by gas chromatography and was found to contain 71% of the desired Compound VI, 8% of the dibromo product, and 20% unreacted 4-methylbenzophenone. After cooling, the reaction mixture was washed with 10 g of sodium bisulfite in 100 ml of water, followed by washing with 3×200 ml of water. The product was dried over sodium sulfate and recrystallized twice from 1:3 toluene : hexane. After drying under vacuum, 635 g of Compound VI were isolated, providing a yield of 60% and having a melting point of 112°–114° C. Analysis on an NMR spectrometer was consistent with the desired product: $^1$H NMR (CDCl$_3$) aromatic protons 7.20–7.80 (m, 9 H) and benzylic protons 4.48 (s, 2 H). The final compound was stored for use in the preparation of a photoactivatable chain transfer agent as described in Example 7.

Example 7

Preparation of N-(2-Mercaptoethyl)-3.5-bis(4-benzoylbenzyloxy)benzamide (Compound VII)

3,5-Dihydroxybenzoic acid, 46.2 g (0.30 mol), was weighed into a 250 ml flask equipped with a Soxhlet extractor and condenser. Methanol, 48.6 ml, and concentrated sulfuric acid, 0.8 ml, were added to the flask and 48 g of 3 A molecular sieves were placed in the Soxhlet extractor. The extractor was filled with methanol and the mixture was heated at reflux overnight. Gas chromatographic analysis of the resulting product showed a 98% conversion to the desired methyl ester. The solvent was removed under reduced pressure to give approximately 59 g of crude product. The product was used in the following step without further purification. A small sample was previously purified for NMR analysis, resulting in a spectrum consistent with the desired product: $^1$H NMR (DMSO-d$_6$) aromatic protons 6.75 (d, 2 H) and 6.38 (t, 1 H), and methyl ester 3.75 (s, 3 H).

The entire methyl ester product from above was placed in a 2 liter flask with an overhead stirrer and condenser, followed by the addition of 173.25 g (0.63 mol) of Compound VI, prepared according to the general method described in Example 6, 207 g (1.50 mol) of potassium carbonate, and 1200 ml of acetone. The resulting mixture was then refluxed overnight to give complete reaction as indicated by thin layer chromatography (TLC). The solids were removed by filtration and the acetone was evaporated under reduced pressure to give 49 g of crude product. The solids were diluted with 1 liter of water and extracted with 3×1 liter of chloroform. The extracts were combined with the acetone soluble fraction and dried over sodium sulfate, yielding 177 g of crude product. The product was recrystallized from acetonitrile to give 150.2 g of a white solid, a 90% yield for the first two steps. Melting point of the product was 131.5° C. (DSC) and analysis on an NMR spectrometer was consistent with the desired product: $^1$H NMR (CDCl$_3$) aromatic protons 7.25–7.80 (m, 18 H), 7.15 (d, 2 H), and 6.70 (t, 1 H), benzylic protons 5.05 (s, 4 H), and methyl ester 3.85 (s, 3 H).

The methyl 3,5-bis(4-benzoylbenzyloxy)benzoate, 60.05 g (0.108 mol), was placed in a 2 liter flask, followed by the addition of 120 ml of water, 480 ml of methanol, and 6.48 g (0.162 mol) of sodium hydroxide. The mixture was heated at reflux for three hours to complete hydrolysis of the ester. After cooling, the methanol was removed under reduced pressure and the sodium salt of the acid was dissolved in 2400 ml of warm water. The acid was precipitated using concentrated hydrochloric acid, filtered, washed with water, and dried in a vacuum oven to give 58.2 g of a white solid (99% yield). Melting point on the product was 188.3° C. (DSC) and analysis on an NMR spectrometer was consistent with the desired product: $^1$H NMR (DMSO-d$_6$) aromatic protons 7.30–7.80 (m, 18 H), 7.15 (d, 2 H), and 6.90 (t, 1 H), and benzylic protons 5.22 (s, 4 H).

The 3,5-bis(4-benzoylbenzyloxy)benzoic acid, 20.0 g (36.86 mmol), was added to a 250 ml flask, followed by 36 ml of toluene, 5.4 ml (74.0 mmol) of thionyl chloride, and 28 μl of N,N-dimethylformamide. The mixture was refluxed for four hours to form the acid chloride. After cooling, the solvent and excess thionyl chloride were removed under reduced pressure. Residual thionyl chloride was removed by four additional evaporations using 20 ml of chloroform each. The crude material was recrystallized from toluene to give 18.45 g of product, an 89% yield. Melting point on the product was 126.9° C. (DSC) and analysis on an NMR spectrometer was consistent with the desired product: $^1$H NMR (CDCl$_3$) aromatic protons 7.30–7.80 (m, 18 H), 7.25 (d, 2 H), and 6.85 (t, 1 H), and benzylic protons 5.10 (s, 4 H).

The 2-aminoethanethiol hydrochloride, 4.19 g (36.7 mmol), was added to a 250 ml flask equipped with an overhead stirrer, followed by 15 ml of chloroform and 10.64 ml (76.5 mmol) of triethylamine. After cooling the amine solution on an ice bath, a solution of 3,5-bis(4-benzoylbenzyloxy)benzoyl chloride, 18.4 g (32.8 mmol), in 50 ml of chloroform was added dropwise over a 50 minute period. Cooling on ice was continued 30 minutes, followed by warming to room temperature for two hours. The product was diluted with 150 ml of chloroform and washed with 5×250 ml of 0.1N hydrochloric acid. The product was dried over sodium sulfate and recrystallized twice from 15:1 toluene: hexane to give 13.3 g of product, a 67% yield. Melting point on the product was 115.9° C.(DSC) and analysis on an NMR spectrometer was consistent with the desired product.: $^1$H NMR (DMSO-d$_6$) aromatic protons 7.20–7.80 (m, 18 H), 6.98 (d, 2 H), and 6.65 (t, 1 H), amide NH 6.55 (broad t, 1 H), benzylic protons 5.10 (s, 4 H), methylene adjacent to amide N 3.52 (q, 2 H), methylene adjacent to SH 2.10 (q, 2 H), and SH 1.38 (t, 1 H). The final compound was stored for use as a chain transfer agent in the synthesis of photoactivatable polymers as described, for instance, in Example 12.

Example 8

Preparation of N-Succinimidyl 11 -(4-Benzoylbenzamido)undecanoate (BBA-AUD-NOS) (Compound VIII)

Compound I (50 g, 0.204 mol), prepared according to the general method described in Example 1, was dissolved in 2500 ml of chloroform, followed by the addition of a solution of 43.1 g (0.214 mol) of 11-aminoundecanoic acid and 60.0 g (1.5 mol) of sodium hydroxide in 1500 ml of water. The mixture was stirred vigorously for one hour in a 5 liter Morton flask to insure thorough mixing of the two layers. The mixture was acidified with 250 ml of concentrated hydrochloric acid and stirred an additional 30 minutes. The organic layer was separated and the aqueous was extracted with 3×500 ml of chloroform. The combined organic extracts were dried over sodium sulfate, filtered, and evaporated to give a solid. The product was recrystallized from toluene to give 68.37 g (82%) of 11-(4-benzoylbenzamido)undecanoic acid with a melting point of 107°–109° C. Analysis on an NMR spectrometer was consistent with the desired product: $^1$H NMR (CDCl$_3$) aromatic protons 7.20–7.80 (m, 9 H), amide NH 6.30 (broad t, 1 H), methylene adjacent to amide N 3.35 (m, 2 H), methylene adjacent to carbonyl 2.25 (t, 2 H), and remaining methylenes 1.00–1.80 (m, 16 H).

The 11-(4-benzoylbenzamido)undecanoic acid, 60.0 g (0.146 mol), was dissolved with warming in 1200 ml of anhydrous 1,4-dioxane in an oven-dried 2000 ml flask. After cooling to room temperature, 17.7 g ( 0.154 mol) of N-hydroxysuccinimide and 33.2 g (0.161 mol) of 1,3-dicyclohexylcarbodiimide were added to the solution and the mixture was stirred overnight under a dry atmosphere. The solids were then removed by filtration, rinsing the filter cake with 1,4 -dioxane. The solvent was then removed under vacuum and the product was recrystallized twice from ethanol. After thorough drying in a vacuum oven, 53.89 g (73% yield) of a white solid were obtained with a melting point of 97°–99° C. Analysis on an NMR spectrometer was consistent with the desired product: $^1$H NMR (CDCl$_3$) aromatic protons 7.20–7.80 (m, 9 H), amide NH 6.25 (broad t, 1 H), methylene adjacent to amide N 3.35 (m, 2 H), methylenes on succinimidyl ring 2.75 (s, 4 H), methylene adjacent to carbonyl 2.55 (t, 2 H), and remaining methylenes 1.00–1.90 (m, 16 H).

Example 9

Preparation of Copolymer of Acrylamide, BBA-APMA, and MAL-EAC-NOS (Random Photo PA-PolyNOS) (Compounds IX, A-C)

A photoactivatable copolymer of the present invention was prepared in the following manner. Acrylamide, 4.298 g (60.5 mmol), was dissolved in 57.8 ml of tetrahydrofuran (THF), followed by 0.219 g ( 0.63 mmol) of Compound III, prepared according to the general method described in Example 3, 0.483 g (1.57 mmol) of Compound IV, prepared according to the general method described in Example 4, 0.058 ml (0.39 mmol) of N,N,N',N'-tetramethylethylenediamine (TEMED), and 0.154 g (0.94 mmol) of 2,2'-azobisisobutyronitrile (AIBN). The solution was deoxygenated with a helium sparge for 3 minutes, followed by an argon sparge for an additional 3 minutes. The sealed vessel was then heated overnight at 60° C. to complete the polymerization. The solid product was isolated by filtration and the filter cake was rinsed thoroughly with THF and CHCl$_3$. The product was dried in a vacuum oven at 30° C. to give 5.34 g of a white solid. NMR analysis (DMSO-d$_6$) confirmed the presence of the NOS group at 2.75 ppm and the photogroup load was determined to be 0.118 mmol BBA/g of polymer. The MAL-EAC-NOS composed 2.5 mole % of the polymerizable monomers in this reaction to give Compound IX-A.

The above procedure was used to prepare a polymer having 5 mole % Compound IV. Acrylamide, 3.849 g (54.1 mmol), was dissolved in 52.9 ml of THF, followed by 0.213 g ( 0.61 mmol) of Compound VI, prepared according to the general method described in Example 3, 0.938 g (3.04 mmol) of Compound IV, prepared according to the general method described in Example 4, 0.053 ml (0.35 mmol) of TEMED and 0.142 g (0.86 mmol) of AIBN. The resulting solid, Compound IX-B, when isolated as described above, gave 4.935 g of product with a photogroup load of 0.101 mmol BBA/g of polymer.

The above procedure was used to prepare a polymer having 10 mole % Compound IV. Acrylamide, 3.241 g (45.6 mmol), was dissolved in 46.4 ml of THF, followed by 0.179 g ( 0.51 mmol) of Compound III, prepared according to the general method described in Example 3, 1.579 g (5.12 mmol) of Compound IV, prepared according to the general method described in Example 4, 0.047 ml (0.31 mmol) of TEMED and 0.126 g (0.77 mmol) of AIBN. The resulting solid, Compound IX-C, when isolated as described above, gave 4.758 g of product with a photogroup load of 0.098 mmol BBA/g of polymer.

Example 10

Preparation of Copolymer of Acrylamide, BBA-APMA, and [3-(Methacryloylamino)propyl] trimethylammonium Chloride (Random Photo PA-PolyQuat) (Compounds X, A-B)

A photoactivatable copolymer of the present invention was prepared in the following manner. Acrylamide, 10.681 g (0.150 mol), was dissolved in 150 ml of dimethylsulfoxide (DMSO), followed by 0.592 g (1.69 mmol) of Compound III, prepared according to the general method described in Example 3, 3.727 g (16.90 mmol) of [3-(methacryloylamino)propyl]trimethylammonium chloride (MAPTAC), delivered as 7.08 ml of a 50% aqueous solution, 0.169 ml (1.12 mmol) of TEMED and 0.333 g (2.03 mmol) of AIBN. The solution was deoxygenated with a helium sparge for 4 minutes, followed by an argon sparge for an additional 4 minutes. The sealed vessel was then heated overnight at 55° C. to complete the polymerization. The DMSO solution was diluted with water and dialyzed against deionized water using 12,000–14,000 molecular weight cutoff tubing. Lyophilization of the resulting solution gave 14.21 g of a white solid. NMR analysis (D$_{2O}$) confirmed the presence of the methyl groups on the quaternary ammonium groups at 3.10 ppm and the photogroup load was determined to be 0.101 mmol BBA/g of polymer. The Compound III constituted 1 mole % of the polymerizable monomer in this reaction to give Compound X-A.

The above procedure was used to prepare a polymer having 2 mole % of Compound III. Acrylamide, 10.237 g (0.144 mol), was dissolved in 145 ml of DMSO, followed by 1.148 g (3.277 mmol) of Compound III, prepared according to the general method described in Example 3, 3.807 g (17.24 mmol) of MAPTAC, delivered as 7.23 ml of a 50% aqueous solution, 0.164 ml (1.09 mmol) of TEMED and 0.322 g (1.96 mmol) of AIBN. Workup as described above gave 12.54 g of product (Compound X-B) with a photogroup load of 0.176 mmol BBA/g of polymer.

Example 11

Preparation of Copolymer of Acrylamide, BBA-APMA, MA-EAC-NOS, and [3-(Methacryloylamino)propyl]trimethylammonium Chloride (Random Photo PA-PolyNOS-PolyQuat) (Compound XI)

A photoactivatable copolymer of the present invention was prepared in the following manner. The water in the commercially available 50% aqueous MAPTAC was removed by azeotropic distillation with chloroform. The aqueous MAPTAC solution, 20 ml containing 10.88 g of MAPTAC, was diluted with 20 ml of DMSO and 100 ml of chloroform. This mixture was refluxed into a heavier-than-water liquid-liquid extractor containing anhydrous sodium sulfate for a total of 80 minutes. A slow flow of air was maintained during the reflux to inhibit polymerization of the monomer. At the end of the reflux, the excess chloroform was removed under reduced pressure to leave a DMSO solution of MAPTAC at an approximate concentration of 352 mg/ml.

Acrylamide, 1.7 g (23.90 mmol), was dissolved in 57.7 ml of dimethylsulfoxide (DMSO), followed by 0.215 g (0.614 mmol) of Compound III, prepared according to the general method described in Example 3, 1.93 ml (0.677 g, 3.067 mmol) of the above MAPTAC/DMSO solution, 0.91 g (3.068 mmol) of Compound V, prepared according to the general method described in Example 5, and 0.060 g (0.365 mmol) of AIBN. The solution was deoxygenated with a helium sparge for 4 minutes, followed by an argon sparge for an additional 4 minutes. The sealed vessel was then heated overnight at 55° C. to complete the polymerization. The polymer was isolated by pouring the reaction mixture into 600 ml of diethyl ether. The solids were separated by centrifuging and the product was washed with 200 ml of diethyl ether and 200 ml of chloroform. Evaporation of solvent under vacuum gave 3.278 g of product with a photoload of 0.185 mmol BBA/g of polymer.

Example 12

Copolymer of Acrylamide and MAL-EAC-NOS using N-(2-Mercaptoethyl)-3,5-bis(4-benzoylbenzyloxy)benzamide (End-point Diphoto PA-PolyNOS) (Compound XII)

A photoactivatable copolymer of the present invention was prepared in the following manner. Acrylamide, 3.16 g (44.5 mmol), was dissolved in 45.0 ml of tetrahydrofuran, followed by 0.164 g (1 mmol) of AIBN, 0.045 ml (0.30 mmol) of TEMED, 0.301 g (0.5 mmol) of Compound VII, prepared according to the general method in Example 7, and 1.539 g (5 mmol) of Compound IV, prepared according to the general method described in Example 4. The solution was deoxygenated with a helium sparge for 4 minutes, followed by an argon sparge for an additional 4 minutes. The sealed vessel was then heated overnight at 55° C. to complete the polymerization. The precipitated polymer was isolated by filtration and was washed with chloroform. The final product was dried in a vacuum oven to provide 4.727 g of polymer having a photogroup load of 0.011 mmol BBA/g of polymer.

Example 13

Copolymer of N-[3-(Dimethylamino)propyl]methacrylamide and BBA-APMA (Random Photo PA-Poly Tertiary Amine) (Compound XIII)

A photoactivatable copolymer of the present invention was prepared in the following manner. N-[3-(Dimethylamino)propyl]methacrylamide, 33.93 g (0.2 mol), was dissolved in 273 ml of DMSO, followed by 16.6 ml of concentrated HCl and 6.071 g (17.3 mmol) of Compound III, prepared according to the general method described in Example 3. Finally, 0.29 ml (1.93 mmol) of TEMED, 0.426 g (2.6 mmol) of AIBN, and 100 ml of water were added to the reaction mixture. The solution was deoxygenated with a helium sparge for 10 minutes and the head space was then filled with argon. The sealed vessel was heated overnight at 55° C. to complete the polymerization. The product was then dialyzed against deionized water for several days using 12,000–14,000 MWCO tubing. The product was filtered following dialysis to remove any solids and was lyophilized to give 47.27 g of a solid product. The polymer was determined to have a photoload of 0.33 mmol BBA/g of polymer.

Example 14

Comparison of Random Photo PA-PolyNOS (Compound IX-C) with Random Photo PA-PolyNOS-PolyQuat (Compound XI) on Polystyrene (PS) Microwell Plates Compound IX-C and Compound XI were separately dissolved in deionized water at 5 mg/ml. The PS plates (PS, Medium Bind, Corning Costar, Cambridge, Mass.) containing 100 μl of Compound IX and Compound XI in separate wells were illuminated with a Dymax lamp (model no. PC-2, Dymax Corporation, Torrington, Conn.) which contained a Heraeus bulb (W. C. Heraeus GmbH, Hanau, Federal Republic of Germany). The illumination duration was for 1.5 minutes at a intensity of 1–2 mW/cm$^2$ in the wavelength range of 330–340 run. The coating solution was then discarded and the wells were air dried for two hours. The plates were then illuminated for an additional one minute. The coated plates were used immediately to immobilize oligos stored in a sealed pouch for up to 2 months.

The 50 base oligomer (-mer) capture probe 5'-NH$_2$-GTCTGAGTCGGAGCCAGGGCGGC CGCCAACAGCAGGAGCAGCGTGCACGG-3'(ID 1) (synthesized with a 5'-amino-modifier containing a C-12 spacer) at 10 pmoles/well was incubated in PS wells in 50 mM phosphate buffer, pH 8.5, 1 mM EDTA at 37° C. for one hour. The hybridization was performed as follows using the complementary 5'-Biotin-CCGTGCACGCTGCTCCTGCTGTTGGCG-GCCGCCCTGGCTCCGACTC AGAC -3'(ID 3) detection probe or non-complementary 5'-Biotin-CGGTGGATGGAGCAGGAGGGGCCC GAGTATTGG-GAGCGGGAGACA CAGAA -3'(ID 4) oligo, both of which were synthesized with a 5'-biotin modification.

The plates with immobilized capture probe were washed with phosphate buffered saline (PBS, 10 mM Na$_2$PO$_{4, 150}$ mM NaCl, pH 7.2) containing 0.05% Tween 20 using a Microplate Auto Washer (model EL 403H, Bio-Tek Instruments, Winooski, Vt.). The plates were then blocked at 55° C. for 30 minutes with hybridization buffer, which consisted of 5×SCC (0.75M NaCl, 0.075M citrate, pH 7.0), 0.1% lauroylsarcosine, 1% casein, and 0.02% sodium dodecyl sulfate. When the detection probe was hybridized to the capture probe, 50 fmole of detection probe in 100 μl were added per well and incubated for one hour at 55° C. The plates were then washed with 2×SSC containing 0.1% sodium dodecyl sulfate for 5 minutes at 55° C. The bound detection probe was assayed by adding 100 μl of a conjugate of streptavidin and horseradish peroxidase (SA-HRP, Pierce, Rockford, Ill.) at 0.5 μg/ml and incubating for 30 minutes at 37° C. The plates were then washed with PBS/Tween, followed by the addition of peroxidase substrate (H$_2$O$_2$ and tetramethylbenzidine, Kirkegard and Perry Laboratories, Gaithersburg, Md.) and measurement at 655 nm on a microwell plate reader (model 3550, Bio-Rad Labs, Cambridge, Mass.). The plates were read at 10 minutes.

The results listed in Table 1 indicate that microwell plates coated with Compound IX-C did not effectively immobilize amine-capture probes. However, by comparison Compound XI, as a coating, provided significant binding and good hybridization signals. Compound IX-C reagent most likely passivated the surfaces and prevented the association of capture oligos. In contrast when Compound XI was used, the oligo was attracted to the surface by ionic interactions where it could then be covalently bonded with the NOS groups.

TABLE 1

Hybridization Signals ($A_{655}$) from PS microwell plates coated with Compound IX-C and Compound XI.

|  | Compound IX-C | Compound XI |
|---|---|---|
| Complementary Detection Probe | 0.187 ± 0.031 | 1.666 ± 0.064 |
| Non-complementary Detection Probe | 0.127 ± 0.016 | 0.174 ± 0.005 |

Example 15

Coating of Various Microwell Plates with a Mixture of Random Photo PA-PolyNOS (Compound IX-B) and Random Photo PA-PolyQuat (Compound X-B)

A coating solution containing a mixture of 5 mg/ml of Compound IX-B and 0.5 mg/ml of Compound X-B was prepared in deionized water. This mixture was used to treat polypropylene (PP, Corning Costar, Cambridge, Mass.), PS, polycarbonate (PC, Corning Costar, Cambridge, Mass.) and polyvinyl chloride (PVC, Dynatech, Chantilly, Va.) multi-wells as described in Example 14. A 30-mer capture oligo 5'-NH$_2$-GTCTGAGTCGGAGCCAGGGCGGCCGCCAAC -3'(ID2), (synthesized with a 5'-amino-modifier containing a C-12 spacer) at 0.03, 0.1, 0.3, 1, 3, or 10 pmole/well was incubated at 4° C. overnight. The hybridization was performed as previously described in Example 14 using complementary ID 3 detection oligo or non-complementary ID 4 oligo. Since PP plates are not optically transparent, the contents of each well were transferred to PS wells after a 20 minute incubation with the chromogenic substrate. The hybridization signals were measured in the PS plates. The other plates were read without transferring at 10 minutes. Signal levels are only comparable within the same substrate group due to the different geometries of microwell plates made from different materials. Table 2 lists the hybridization signals and shows the relationship between the intensity of the hybridization signals and the amount of capture probe applied to various microwell plates coated with a mixture of Compound IX-B and Compound X-B. On PP and PVC plates, adsorption of probes was very low and the coatings with the polymeric reagents improved the signals dramatically. The signal increased with increasing capture probe added to the coated wells, but leveled off at approximately 3 pmole/well capture. The plateau in the amount of signal generated was not due to a saturating level of hybridization, but rather to the limits of the color change reaction in the calorimetric assay.

Oligo derivatives adsorb efficiently onto uncoated PS and PC microwell plates and result in specific hybridization signals. Cros et al. (U.S. Pat. No. 5,510,084) also reported that amine-functionalized oligos adsorbed satisfactorily onto polystyrene microwell plates by 10 unknown mechanisms. However, there is marked variability in the amount of adsorption on uncoated PS plates among different lots (Chevier et al. *FEMS* 10:245, 1995).

TABLE 2

Hybridization signals ($A_{655}$) from various microwell plate materials coated with a mixture of Compound IX-B and Compound X-B.

| | Capture Oligo Added (pmole/well) | | | | | | | | | | | |
|---|---|---|---|---|---|---|---|---|---|---|---|---|
| | 0.03 | | 0.1 | | 0.3 | | 1 | | 3 | | 10 | |
| | Comp | NC | Comp | NC | Comp | NC | Comp | NC | Comp | NC | Comp | NC |
| PP | | | | | | | | | | | | |
| Uncoated | 0.083 | 0.082 | 0.076 | 0.072 | 0.076 | 0.074 | 0.088 | 0.074 | 0.070 | 0.067 | 0.078 | 0.073 |
| Coated | 0.541 | 0.099 | 1.070 | 0.099 | 1.769 | 0.091 | 2.283 | 0.094 | 2.582 | 0.141 | 2.490 | 0.320 |
| PVC | | | | | | | | | | | | |
| Uncoated | 0.074 | 0.079 | 0.081 | 0.075 | 0.097 | 0.078 | 0.137 | 0.076 | 0.215 | 0.081 | 0.337 | 0.092 |
| Coated | 0.423 | 0.116 | 0.875 | 0.110 | 1.326 | 0.112 | 1.583 | 0.142 | 1.628 | 0.186 | 1.604 | 0.332 |
| PS | | | | | | | | | | | | |
| Uncoated | 0.235 | 0.099 | 0.435 | 0.091 | 0.827 | 0.090 | 1.205 | 0.093 | 1.380 | 0.093 | 1.404 | 0.136 |
| Coated | 0.435 | 0.121 | 0.801 | 0.105 | 1.177 | 0.116 | 1.401 | 0.132 | 1.470 | 0.132 | 1.487 | 0.302 |
| PC | | | | | | | | | | | | |
| Uncoated | 0.676 | 0.248 | 1.364 | 0.244 | 2.103 | 0.256 | 2.701 | 0.266 | 2.745 | 0.295 | 2.930 | 0.388 |
| Coated | 1.034 | 0.327 | 1.602 | 0.306 | 2.136 | 0.295 | 2.218 | 0.287 | 2.380 | 0.342 | 2.500 | 0.572 |

Comp.: Complementary detection probe was added for hybridization.
NC: Non-complementary detection probe was added for hybridization.

Example 16

Evaluation of End-point Diphoto PA-polyNOS (Compound XII) and Random Photo PA-PolyQuat (Compound X-B) on PP and PVC Microwell Plates A coating solution containing a mixture of 5 mg/ml of Compound XII and 0.5 mg/ml of Compound X-B was prepared with deionized water. This mixture of the two reagents was used to coat PP and PVC microwell plates under conditions comparable to those described in Example 14. The 30-mer ID 2 capture oligo at 0.03, 0.1, 0.3, 1, 3, or 10 pmole/well in 0.1 ml was incubated at 4° C. overnight. The hybridization was performed as described in Example 14 using complementary ID 3 detection oligo or non-complementary ID 4 oligo. The hybridization signals listed in Table 3 demonstrate the relationship between the intensity of the hybridization signals and the amount of capture probe applied to PP and PVC microwell plates coated with a mixture of Compound XII and Compound X-B. The signal increased with increasing capture oligos added to the coated wells, but leveled off at approximately 1 pmole/well. The signal-to-noise ratio (from complementary vs. non-complementary detection probes) was as high as 26 and 11 for coated PP and PVC surfaces, respectively.

14 using complementary ID 3 detection oligo or non-complementary ID 4 oligo. Table 4 contains the hybridization signals and shows the relationship between the intensity of the hybridization signals and the amount of capture probe applied to PP and PVC microwell plates coated with Compound X-B followed by Compound VIII coating. The signal increased with increasing capture probe added to the coated wells, but leveled off at approximately 1 pmole/well capture oligo. The signals were up to 29- and 11- fold higher for coated PP and PVC surfaces, respectively, as compared to the uncoated controls.

TABLE 3

Hybridization signals ($A_{655}$) from PP and PVC plates coated with mixture of Compound XII and Compound X-B.

| pmole/well | PP Microwell plates | | PVC Microwell plates | |
| --- | --- | --- | --- | --- |
| Capture Added | Comp. Detection | Non-comp. | Comp. Detection | Non-comp. |
| 0.03 | 0.153 ± 0.008 | 0.070 ± 0.007 | 0.289 ± 0.029 | 0.094 ± 0.020 |
| 0.1 | 0.537 ± 0.042 | 0.075 ± 0.009 | 0.759 ± 0.054 | 0.104 ± 0.014 |
| 0.3 | 1.206 ± 0.106 | 0.080 ± 0.003 | 1.262 ± 0.023 | 0.117 ± 0.011 |
| 1 | 2.157 ± 0.142 | 0.081 ± 0.003 | 1.520 ± 0.044 | 0.189 ± 0.064 |
| 3 | 2.624 ± 0.162 | 0.108 ± 0.012 | 1.571 ± 0.031 | 0.179 ± 0.016 |
| 10 | 2.921 ± 0.026 | 0.200 ± 0.018 | 1.625 ± 0.040 | 0.286 ± 0.021 |

Example 17

Sequential Coating with Random Photo PA-PolyQuat (Compound X-B) and BBA-AUD-NOS (Compound VIII)

Compound X-B at 0.1 mg/ml in deionized water was incubated in PP and PVC wells for 20 minutes. The plates were illuminated as previously described in Example 14 with the solution in the wells for 1.5 minutes. The solution was discarded and the wells were dried. Compound VIII at 0.5 mg/ml in isopropyl alcohol (IPA) was incubated in the Compound X-B coated wells for 5 minutes. The solution was then removed, the plate dried and illuminated as described in Example 14 for one minute after the wells were dried. The 30-mer ID 2 capture oligo at 0.03, 0.1, 0.3, 1, 3, or 10 pmole/well in 0.1 ml was incubated at 4° C. overnight. The hybridization was performed as described in Example

TABLE 4

Hybridization signals ($A_{655}$) from PP and PVC microwell plates coated with Compound X-B followed by Compound VIII coating.

| pmole/well | PP Microwell plates | | PVC Microwell plates | |
| --- | --- | --- | --- | --- |
| Capture Added | Uncoated | Coated | Uncoated | Coated |
| 0.03 | 0.083 ± 0.003 | 0.157 ± 0.004 | 0.074 ± 0.004 | 0.244 ± 0.014 |
| 0.1 | 0.076 ± 0.003 | 0.544 ± 0.006 | 0.081 ± 0.005 | 0.694 ± 0.065 |
| 0.3 | 0.076 ± 0.006 | 1.095 ± 0.015 | 0.097 ± 0.010 | 1.113 ± 0.033 |
| 1 | 0.088 ± 0.006 | 1.676 ± 0.030 | 0.137 ± 0.016 | 1.304 ± 0.027 |
| 3 | 0.070 ± 0.010 | 1.865 ± 0.057 | 0.215 ± 0.023 | 1.237 ± 0.013 |
| 10 | 0.078 ± 0.009 | 2.274 ± 0.005 | 0.337 ± 0.024 | 1.182 ± 0.041 |

Example 18

Comparision of Random Photo PA-PolyQuat (Compound X-A) with a Mixture of Random Photo PA-PolyNOS (Compound IX-A) and Random Photo PA-PolyQuat (Compound X-A)

Compound X-A at 0.5 or 0.1 mg/ml was incubated in PP microwell plates for 10 minutes. The plates were then illuminated as described in Example 14. A coating solution containing a mixture of Compound IX-A and Compound X-A was prepared at two ratios, 5/0.5 mg/ml and 0.5/0.1 mg/ml of Compound IX-A/Compound X-A in deionized water to coat PP microwell plates. The solution was incubated in the wells for 10 minutes and the wells were illuminated as described in Example 14. The 30-mer ID 2 capture oligo at 1 pmole/well was incubated in each well at 37° C. for one hour. The hybridization was done as described in Example 14 using complementary ID 3 detection oligo or non-complementary ID 4 oligo. The results listed in Table 5 indicate that the coating containing the combination of Compound IX-A and Compound X-A gave higher signals as compared to those from Compound X-A coating alone.

oligo without the 5'-amine modification was used as the capture probe on Compound IX-B/Compound X-B coated surfaces, the hybridization signal was less than 30% of that with amine modification.

TABLE 6

Signals ($A_{655}$) generated from hybridization reactions with either ID 5 or ID 6 oligos on Compound IX-B/Compound X-B coated microwell plates.

| | No Capture Added | | Non-modified Capture | | Amine-modified Capture | |
|---|---|---|---|---|---|---|
| | Comp. Detection | Non-comp. Detection | Comp. Detection | Non-comp. Detection | Comp. Detection | Non-comp. Detection |
| PP | | | | | | |
| Uncoated | 0.032 ± 0.001 | 0.036 ± 0.004 | 0.033 ± 0.001 | 0.036 ± 0.001 | 0.037 ± 0.005 | 0.033 ± 0.001 |
| Coated | 0.038 ± 0.002 | 0.040 ± 0.001 | 0.555 ± 0.041 | 0.044 ± 0.001 | 1.915 ± 0.029 | 0.066 ± 0.003 |
| PVC | | | | | | |
| Uncoated | 0.248 ± 0.049 | 0.176 ± 0.008 | 0.259 ± 0.049 | 0.128 ± 0.013 | 0.404 ± 0.100 | 0.118 ± 0.025 |
| Coated | 0.115 ± 0.027 | 0.090 ± 0.014 | 0.379 ± 0.028 | 0.091 ± 0.014 | 1.319 ± 0.027 | 0.101 ± 0.017 |
| PS | | | | | | |
| Uncoated | 0.084 ± 0.013 | 0.089 ± 0.014 | 0.668 ± 0.047 | 0.085 ± 0.023 | 1.269 ± 0.034 | 0.106 ± 0.024 |
| Coated | 0.080 ± 0.006 | 0.081 ± 0.023 | 0.364 ± 0.010 | 0.089 ± 0.015 | 1.437 ± 0.012 | 0.098 ± 0.005 |

TABLE 5

Hybridization signals ($A_{655}$) from Compound X-A coated PP microwell plates.

| Ratio of Compound IX-A/Compound X-A (mg/ml) | Comp. Detection | Non-comp. Detection |
|---|---|---|
| 5/0.5 | 1.436 ± 0.056 | 0.077 ± 0.001 |
| 0/0.5 | 0.454 ± 0.149 | 0.052 ± 0.006 |
| 0.5/0.1 | 1.346 ± 0.044 | 0.062 ± 0.003 |
| 0/0.1 | 0.192 ± 0.082 | 0.055 ± 0.002 |

Example 19

Comparision of Non-modified Oligo vs. Amine-Modified Oligo on Random Photo PA-PolyNOS (Compound IX-B) and Random Photo PA-PolyQuat (Compound X-B) on Coated Microwell A coating solution containing a mixture of Compound IX-B (5 mg/ml) and Compound X-B (0.5 mg/ml) was prepared in deionized water to coat PP, PS and PVC microwell plates. The solution was incubated for approximately 10 minutes and illuminated as described in Example 14. The 30-mer capture 5'-$NH_2$-TTCTGTGTCTCC CGCTCCCAATACTCGGGC-3'(ID 5) oligo at 1 pmole/well was coupled to the wells in 50 mM phosphate buffer, pH 8.5, 1 mM EDTA at 4° C. overnight. The hybridization was performed as described in Example 14 using complementary detection oligo ID 4 or non-complementary oligo ID 3. To determine the effect of the amine-functionality of the capture oligo, a non-modified 30-mer capture probe 5'-TTCTGTGTCTCC CGCTCCCAATACTCGGGC-3'(ID 6) (with no amine) was also added to the coated surfaces and tested. The results shown in Table 6 indicate that when an Example 20

Oligo Loading Densities on Microwell Plates Coated with Random Photo PA-PolyNOS (Compound IX-A) and Random Photo PA-PolyQuat (Compound X-A)

Radiolabeled assays were performed to determine oligo loading densities and to verify results from the calorimetric assay system. In this example, combination coatings of Compound IX-A and Compound X-A were performed on PVC wells as described in example 14. The ID 2 and ID 5 30-mer capture oligos were immobilized on coated wells. A radiolabeled ID 2 probe was used to determine the loading density of immobilized capture oligos on the well surface. A radiolabeled ID 3 detection probe, which was complementary to ID 2, but not to ID 5, was used to measure hybridization reactions of the immobilized capture probes. Oligos ID 2 and ID 3 were radiolabeled at the 3'-end using terminal transferase (Boehringer Mannheim, Indianapolis, Ind.) and α-$^{32}$P-ddATP (3000 Ci/mmole, Amersham, Arlington Heights, Ill.) according to the manufacturer's specifications. $^{32}$P-labeled ID 2 and unlabeled ID 2 and ID 5 capture probes were incubated in coated wells at 50 pmole/well for 2.25 hours at room temperature. The plates were washed and blocked as described in Example 14.

The wells with the unlabeled capture probes were hybridized with the $^{32}$P-labeled ID 3 detection probe in hybridization buffer for 1 hour at 55° C. Wells containing the $^{32}$P-labeled capture probe were incubated in hybridization buffer without the ID 3 probe. After washing three times with 2×SSC containing 0.1% SDS for 5 minutes at 55° C. and three times with PBS/0.05% Tween, the plates were cut into individual wells and dissolved in tetrahydrofuran. The amount of radioactivity in each well was measured by scintillation counting in Aquasol-2 Fluor (DuPont NEN, Boston, Mass.). The results in Table 7 show that both Compound IX-A and Compound X-A were required to give good immobilization of capture probe. Also, increasing the concentrations of Compound IX-A and Compound X-A increased the amount of the capture oligo immobilized. At the highest concentrations tested, the signal to noise ratio was greater than 3000 to 1.

TABLE 7

Densities of Immobilized Capture Oligo and Hybridized $^{32}$P-Detection Oligo.

| Mixture of Coating Reagents | | Immobilized | Hybridized comp. | Hybridized non-comp. |
|---|---|---|---|---|
| Compound IX-A (mg/ml) | Compound X-A (mg/ml) | capture fmole/well | detection fmole/well | detection fmole/well |
| 0 | 0 | 41.3 | 2.3 | 0.6 |
| 0 | 0.05 | 37.5 | 10.9 | 0.7 |
| 0.55 | 0 | 32.6 | 5.4 | 0.6 |
| 1 | 0.1 | 344.1 | 308.8 | 26.4 |
| 0.1 | 0.1 | 285.7 | 222.2 | 55.7 |
| 1 | 0.001 | 52.8 | 26.2 | 0.6 |
| 0.1 | 0.001 | 73.5 | 20.8 | 13.1 |
| 1.19 | 0.05 | 280.4 | 256.9 | 1.1 |
| 0.55 | 0.12 | 401.9 | 379.1 | 0.7 |
| 0.55 | 0.05 | 338.0 | 315.1 | 1.6 |
| 2 | 0.5 | 1633.4 | 1108.4 | 0.3 |

Example 21

Comparision between Random Photo-PA-Polytertiary Amine (Compound XIII), Random Photo-PA-PolyNOS (Compound IX-A) and a Mixture of Random Photo PA-PolyNOS (Compound IX-A) and Random Photo-PA-Polytertiary Amine (Compound XIII)

Compound XIII at 0.02 mg/ml in deionized water was incubated in PP microwell plates for 10 minutes. The wells were illuminated as described in Example 14. Compound IX-A was coated on PP wells at 2 mg/ml in deionized water as described for Compound XIII. A coating solution containing a mixture of 2 mg/ml Compound IX-A and 0.02 mg/ml Compound XIII in deionized water was prepared and coated as described for Compound XIII. The 30-mer ID 2 capture oligo at 5 pmole/well was incubated in each well at 37° C. for one hour. The hybridization was done as described in Example 14 using complementary ID 3 detection oligo and non-complementary ID 4 oligo. The contents of each well were transferred to PS wells after a 10 minute incubation with the peroxidase substrate. The results listed in Table 8 indicate that the combination of Compound IX-A and Compound XIII gave higher signals compared to those from Compound IX-A or Compound XIII coating alone.

TABLE 8

Hybridization signals ($A_{655}$) from coated PP microwell plates.

| Coating | Comp. Detection | Non-comp. Detection |
|---|---|---|
| Compound IX-A | 0.057 ± 0.001 | 0.052 ± 0.006 |
| Compound XIII | 0.746 ± 0.042 | 0.081 ± 0.009 |
| Compound IX-A/Compound XIII Mixture | 1.195 ± 0.046 | 0.078 ± 0.014 |

Example 22

Nucleic Acid Sequence Immobilization on an Amine Derivatized Surface

A copolymer of the present invention is prepared in the following manner. Acrylamide, 5.686 g (80.0 mmol), is dissolved in 100 ml of DMSO, followed by the addition of 3.083 g (10.0 mmol) of Compound IV, prepared according to the general method described in Example 4, and 2.207 g (10.0 mmol) of MAPTAC, delivered as a dry DMSO solution prepared according to the general method described in Example 11. TEMED, 0.134 ml (0.89 mmol), and AIBN, 0.197 g (1.20 mmol), are added to the mixture and the system is deoxygenated with a helium sparge for 5 minutes, followed by an argon sparge for an additional 5 minutes. The sealed vessel is heated at 55° C. to complete the polymerization. The polymer is isolated by pouring the reaction mixture into 800 ml of diethyl ether and centrifuging to separate the solids. The product is washed with 200 ml of diethyl ether, followed by 200 ml of chloroform. The polymer is dried under vacuum to remove remaining solvent.

A polymer surface is derivatized by plasma treatment using a 3:1 mixture of methane and ammonia gases. (See, e.g., the general method described in U.S. Pat. 5,643,580). A mixture of methane (490 SCCM) and ammonia (161 SCCM) are introduced into the plasma chamber along with the polymer part to be coated. The gases are maintained at a pressure of 0.2–0.3 torr and a 300–500 watt glow discharge is established within the chamber. The sample is treated for a total of 3–5 minutes under these conditions. Formation of an amine derivatized surface is verified by a reduction in the water contact angle compared to the uncoated surface.

The amine derivatized surface is incubated for 10 minutes at room temperature with a 10 mg/ml solution of the above polymer in a 50 mM phosphate buffer, pH 8.5. Following this reaction time, the coating solution is removed and the surface is washed thoroughly with deionized water and dried thoroughly. Immobilization of oligomer capture probe and hybridization is performed as described in Example 14.

TABLE 9

Compounds.

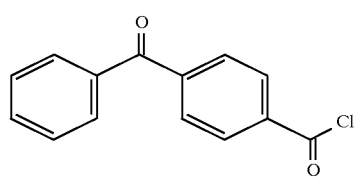

COMPOUND I

TABLE 9-continued

Compounds.

H₂N—(CH₂)₃—NH—C(=O)—C(CH₃)=CH₂ · HCl — COMPOUND II

Ph—C(=O)—C₆H₄—C(=O)—NH—(CH₂)₃—NH—C(=O)—C(CH₃)=CH₂ — COMPOUND III

Maleimide-N—(CH₂)₅—C(=O)—O—N-succinimide — COMPOUND IV

CH₂=C(CH₃)—C(=O)—NH—(CH₂)₅—C(=O)—O—N-succinimide — COMPOUND V

Ph—C(=O)—C₆H₄—CH₂Br — COMPOUND VI

Bis[4-benzoylphenyl-CH₂—O—] substituted benzamide—N(H)—(CH₂)₂—SH — COMPOUND VII

Ph—C(=O)—C₆H₄—C(=O)—NH—(CH₂)₁₀—C(=O)—O—N-succinimide — COMPOUND VIII

TABLE 9-continued
Compounds.
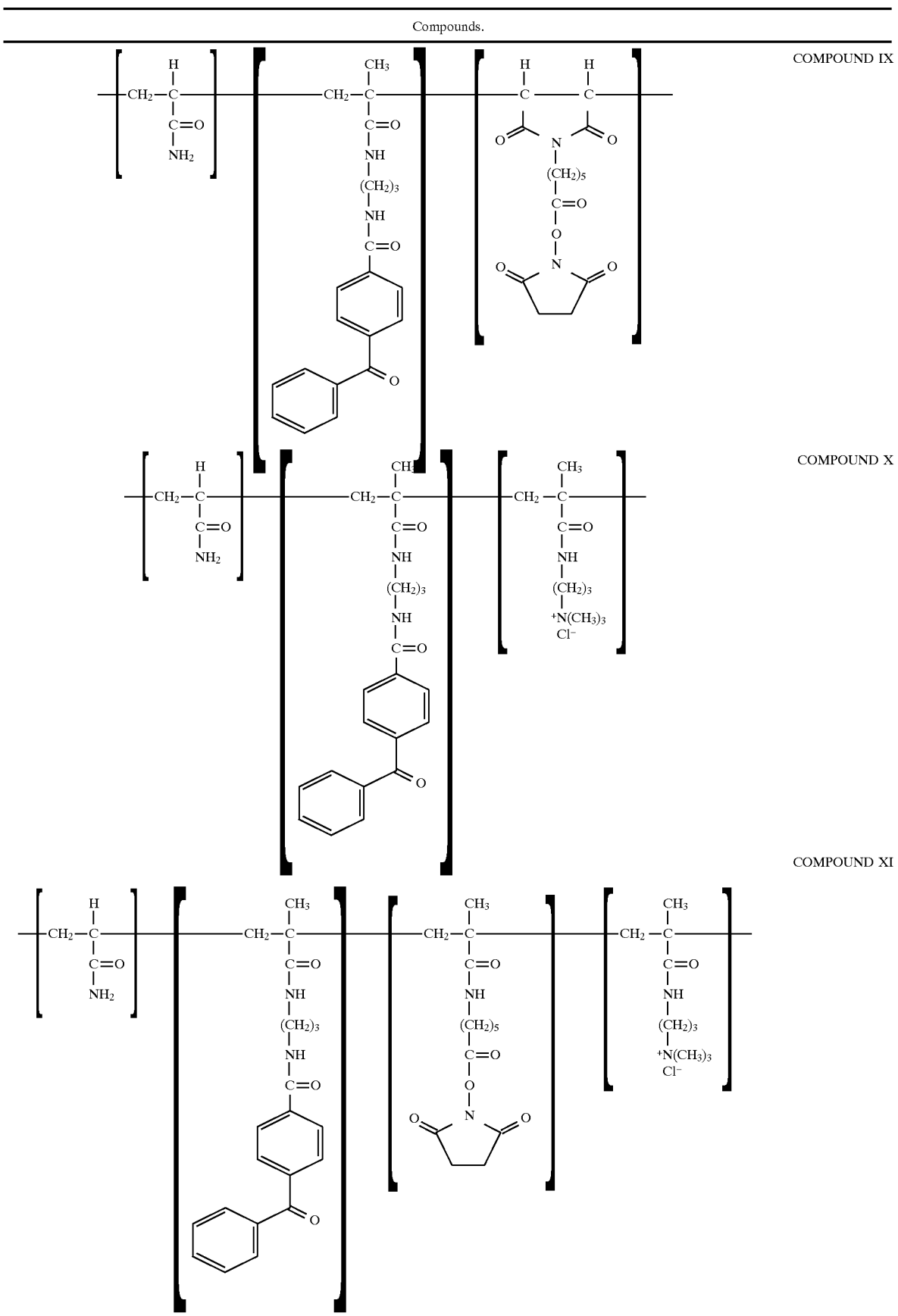
COMPOUND IX
COMPOUND X
COMPOUND XI

TABLE 9-continued

Compounds.

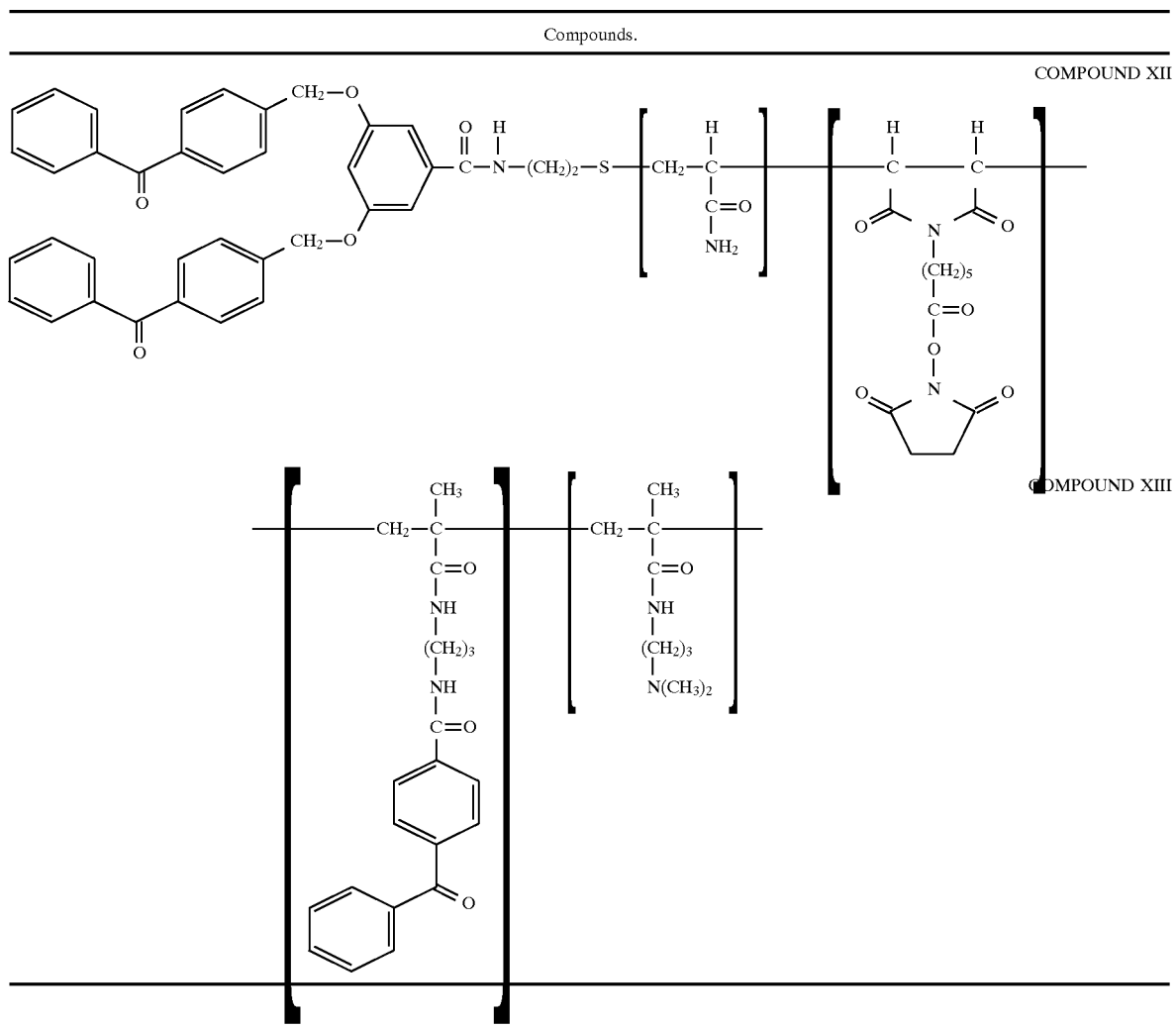

COMPOUND XII

COMPOUND XIII

What is claimed is:

1. A reagent composition for attaching a target molecule to the surface of a substrate, the reagent composition comprising one or more groups for attracting the target molecule to the reagent, and one or more thermochemically amine-reactive or sulfhydryl-reactive groups for forming covalent bonds with corresponding functional groups on the attracted target molecule.

2. A reagent composition according to claim 1 wherein the reagent composition further comprises one or more photoreactive groups for attaching the reagent composition to the surface upon application of energy from a source of electromagnetic radiation.

3. A reagent composition according to claim 1 wherein the attracting groups and thermochemically reactive groups are pendent upon one or more hydrophilic polymeric backbones.

4. A reagent composition according to claim 1 wherein the target molecule is a nucleic acid.

5. A reagent composition according to claim 1 wherein the attracting groups are ionic groups.

6. A reagent composition according to claim 5 wherein the ionic groups are selected from the group consisting of quaternary ammonium groups and protonated tertiary amines.

7. A reagent composition according to claim 4 wherein the nucleic acid comprises a functional group selected from the group consisting of amine and sulfhydryl groups.

8. A reagent composition according to claim 4 wherein the reagent composition comprises a hydrophilic polymeric backbone comprising one or more ionic groups as attracting groups and one or more photoreactive groups for attaching the reagent composition to the surface upon application of energy from a source of electromagnetic radiation.

9. A reagent composition according to claim 8 wherein the ionic groups comprise quaternary ammonium groups.

10. A reagent composition according to claim 2 wherein the photoreactive groups are selected from the group consisting of photoreactive aryl ketones.

11. A reagent composition according to claim 10 wherein the photoreactive aryl ketones are each, independently, selected from the group consisting of acetophenone, benzophenone, anthraquinone, anthrone, and anthrone-like heterocycles.

12. A reagent composition according to claim 2 wherein the target molecule is a nucleic acid, the attracting groups are ionic groups, and the photoreactive groups are selected from the group consisting of photoreactive aryl ketones.

13. A reagent composition according to claim 12 wherein the photoreactive aryl ketones are each, independently, selected from the group consisting of acetophenone, benzophenone, anthraquinone, anthrone, and anthrone-like heterocycles.

14. A reagent composition according to claim 3 wherein the reagent composition is provided in the form of a composition comprising a first reagent component comprising a hydrophilic backbone comprising one or more attractive groups and one or more photoreactive groups, and a second reagent component comprising a hydrophilic backbone comprising one or more thermochemically amine-reactive or sulfhydryl-reactive groups and one or more photoreactive groups.

15. A reagent composition according to claim 14 wherein the target molecule is a nucleic acid.

16. A reagent composition according to claim 14 wherein the attracting groups are ionic groups.

17. A reagent composition according to claim 16 wherein the ionic groups are selected from the group consisting of quaternary ammonium groups and protonated tertiary amines.

18. A reagent composition according to claim 15 wherein the nucleic acid comprises a functional group selected from the group consisting of amine and sulfhydryl groups.

19. A reagent composition according to claim 14 wherein the photoreactive groups are selected from the group consisting of photoreactive aryl ketones.

20. A reagent composition according to claim 19 wherein the photoreactive aryl ketones are each, independently, selected from the group consisting of acetophenone, benzophenone, anthraquinone, anthrone, and anthrone-like heterocycles.

21. A method for attaching a target molecule to the surface of a substrate, the method comprising the steps of (a) providing upon the surface of the substrate a reagent composition comprising one or more groups for attracting the target molecule to the reagent composition, and one or more thermochemically amine-reactive or sulfhydryl-reactive groups for forming covalent bonds with corresponding functional groups on the attracted target molecule, (b) bringing the target molecule into sufficient proximity to the surface to permit the attractive groups to attract the target molecule to the bound reagent composition, and (c) allowing the thermochemically reactive groups to form covalent bonds with the attracted target molecule.

22. A method according to claim 21 wherein the reagent composition further comprises one or more photoreactive groups for attaching the reagent composition to the surface upon application of energy from a source of electromagnetic radiation.

23. A method according to claim 21 wherein the attracting groups and thermochemically reactive groups are pendent upon one or more hydrophilic polymeric backbones.

24. A method according to claim 21 wherein the target molecule is a nucleic acid.

25. A method according to claim 21 wherein the attracting groups are ionic groups.

26. A method according to claim 25 wherein the ionic groups are selected from the group consisting of quaternary ammonium groups and protonated tertiary amines.

27. A method according to claim 24 wherein the nucleic acid comprises a functional group selected from the group consisting of amine and sulfhydryl groups.

28. A method according to claim 24 wherein the reagent composition comprises a hydrophilic polymeric backbone comprising one or more ionic groups as attracting groups and one or more photoreactive groups for attaching the reagent composition to the surface upon application of energy from a source of electromagnetic radiation.

29. A method according to claim 28 wherein the ionic groups comprise quaternary ammonium groups.

30. A method according to claim 22 wherein the photoreactive groups are selected from the group consisting of photoreactive aryl ketones.

31. A method according to claim 30 wherein the photoreactive aryl ketones are each, independently, selected from the group consisting of acetophenone, benzophenone, anthraquinone, anthrone, and anthrone-like heterocycles.

32. A method according to claim 26 wherein the target molecule is a nucleic acid and the photoreactive groups are selected from the group consisting of photoreactive aryl ketones.

33. A method according to claim 32 wherein the photoreactive aryl ketones are each, independently, selected from the group consisting of acetophenone, benzophenone, anthraquinone, anthrone, and anthrone-like heterocycles.

34. A method according to claim 23 wherein the reagent composition is provided in the form of a composition comprising a first reagent component comprising a hydrophilic backbone comprising one or more attractive groups and one or more photoreactive groups, and a second reagent component comprising a hydrophilic backbone comprising one or more thermochemically amine-reactive or sulfhydryl-reactive groups and one or more photoreactive groups.

35. A method according to claim 34 wherein the target molecule is a nucleic acid.

36. A method according to claim 31 wherein the attracting groups are ionic groups.

37. A method according to claim 36 wherein the ionic groups are selected from the group consisting of quaternary ammonium groups and protonated tertiary amines.

38. A method according to claim 35 wherein the nucleic acid comprises a functional group selected from the group consisting of amine and sulfhydryl groups.

39. A method according to claim 34 wherein the photoreactive groups are selected from the group consisting of photoreactive aryl ketones.

40. A method according to claim 39 wherein the photoreactive aryl ketones are each, independently, selected from the group consisting of acetophenone, benzophenone, anthraquinone, anthrone, and anthrone-like heterocycles.

41. A substrate surface coated with a target molecule and a reagent composition by the method of claim 21.

42. A surface according to claim 41 wherein the reagent composition further comprises one or more photoreactive groups for attaching the reagent composition to the surface upon application of energy from a source of electromagnetic radiation.

43. A surface according to claim 42 wherein the target molecule is a nucleic acid.

44. A surface according to claim 41 wherein the attracting groups are ionic groups selected from the group consisting of quaternary ammonium groups and protonated tertiary amines.

45. A surface according to claim 43 wherein the nucleic acid comprises a functional group selected from the group consisting of amine and sulfhydryl groups.

46. A surface according to claim 41 wherein the photoreactive groups are selected from the group consisting of photoreactive aryl ketones.

47. A surface according to claim 46 wherein the photoreactive aryl ketones are each, independently, selected from the group consisting of acetophenone, benzophenone, anthraquinone, anthrone, and anthrone-like heterocycles.

48. A surface according to claim 42 wherein the reagent composition is provided in the form of a composition comprising a first reagent component comprising a hydrophilic backbone comprising one or more attractive groups and one or more photoreactive groups, and a second reagent component comprising a hydrophilic backbone comprising one or more thermochemically amine-reactive or sulfhydryl-reactive groups and one or more photoreactive groups.

49. A surface according to claim 48 wherein the photoreactive groups are selected from the group consisting of photoreactive aryl ketones.

50. A surface according to claim 49 wherein the photoreactive aryl ketones are each, independently, selected from the group consisting of acetophenone, benzophenone, anthraquinone, anthrone, and anthrone-like heterocycles.

51. A surface comprising a coated reagent composition of claim 1.

52. A surface according to claim 51 wherein the reagent composition further comprises one or more photoreactive groups for attaching the reagent composition to the surface upon application of energy from a source of electromagnetic radiation.

53. A surface according to claim 52 wherein the target molecule is a nucleic acid.

54. A surface according to claim 51 wherein the attracting groups are ionic groups selected from the group consisting of quaternary ammonium groups and protonated tertiary amines.

55. A surface according to claim 53 wherein the nucleic acid comprises a functional group selected from the group consisting of amine and sulfhydryl groups.

56. A surface according to claim 51 wherein the photoreactive groups are selected from the group consisting of photoreactive aryl ketones.

57. A surface according to claim 56 wherein the photoreactive aryl ketones are each, independently, selected from the group consisting of acetophenone, benzophenone, anthraquinone, anthrone, and anthrone-like heterocycles.

58. A surface according to claim 52 wherein the reagent composition is provided in the form of a composition comprising a first reagent component comprising a hydrophilic backbone comprising one or more attractive groups and one or more photoreactive groups, and a second reagent component comprising a hydrophilic backbone comprising one or more thermochemically amine-reactive or sulfhydryl-reactive groups and one or more photoreactive groups.

59. A surface according to claim 58 wherein the photoreactive groups are selected from the group consisting of photoreactive aryl ketones.

60. A surface according to claim 59 wherein the photoreactive aryl ketones are each, independently, selected from the group consisting of acetophenone, benzophenone, anthraquinone, anthrone, and anthrone-like heterocycles.

\* \* \* \* \*